United States Patent [19]
Kottenhahn et al.

[11] Patent Number: 6,093,823
[45] Date of Patent: Jul. 25, 2000

[54] PROCESS FOR THE CONTINUOUS PRODUCTION OF BASIC CYCLIC OPTICALLY ACTIVE α- AMINO ACIDS

[75] Inventors: Matthias Kottenhahn, Freigericht; Klaus Stingl, Alzenau; Karlheinz Drauz, Freigericht, all of Germany

[73] Assignee: Degussa Aktiengesellschaft, Frankfurt, Germany

[21] Appl. No.: 09/047,280

[22] PCT Filed: Sep. 18, 1996

[86] PCT No.: PCT/EP96/04073

§ 371 Date: Mar. 24, 1998

§ 102(e) Date: Mar. 24, 1998

[87] PCT Pub. No.: WO97/12881

PCT Pub. Date: Apr. 10, 1997

[30] Foreign Application Priority Data

Sep. 30, 1995 [DE] Germany .............. 195 36 658

[51] Int. Cl.$^7$ .................................. C07D 241/04
[52] U.S. Cl. .............. 544/389; 540/544; 540/575; 540/608; 544/172; 546/245; 548/215; 548/535; 548/334.5

[58] Field of Search .................... 544/389, 172; 540/544, 575, 608; 546/245; 548/215, 334.5, 535

[56] References Cited

FOREIGN PATENT DOCUMENTS

WO 95/21162  8/1995  WIPO .

OTHER PUBLICATIONS

Felder et al., Helvetica Chimica Acta, vol. 43, No. 117, pp. 888–896, 1960.

*Primary Examiner*—Richard L. Raymond
*Attorney, Agent, or Firm*—Omri M. Behr, Esq.

[57] ABSTRACT

The invention pertains to a process for the continuous production of basic cyclic optically active α-amino acids of general formula (I) by continuous racemate splitting via diastereomeric salt pairs with re-racemisation of the residual amino acid or amino acid derivative in the mother liquid with the aid of an optically active acid.

13 Claims, No Drawings

PROCESS FOR THE CONTINUOUS PRODUCTION OF BASIC CYCLIC OPTICALLY ACTIVE α- AMINO ACIDS

RELATED APPLICATIONS

This application is a 371 of PCT/EP96/04073, filed Sep. 18, 1996.

FIELD OF THE APPLICATION

This invention relates to a novel process for the production of basic, cyclic and optically active α-amino acids of the general formula I

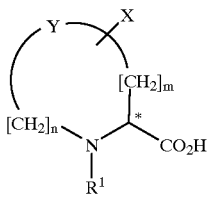

Formula I in which

- n, m may mutually independently be 0, 1, 2 or 3,
- Y may be $CXR^1$ or heteroatoms such as N, O or S, wherein the stated heteroatoms may in turn be substituted with H, ($C_1$–$C_6$) alkyl, benzyl, formyl, $COR^2$, or $CO_2R^3$, benzyl, which may optionally be substituted with hydroxy, fluorine, chlorine, bromine or an $NO_2$ group in position 2, 3 or 4,
- X means H, $NH_2$, OH, F, Cl or Br,
- $R^1$ means H, ($C_1$–$C_6$) alkyl, benzyl, formyl, $COR^2$ or $CO_2R^3$,
- $R^2$ means ($C_1$–$C_6$) alkyl, phenyl, benzyl, $NH_2$, $NO_2$-phenyl or $NO_2$-benzyl,
- $R^3$ means ($C_1$–$C_6$) alkyl, phenyl, benzyl, $NO_2$-phenyl or $NO_2$-benzyl and
- * denotes a carbon atom in R or S configuration.

Chiral α-amino acids of the general formula I are, inter alia, important building blocks for the pharmaceuticals industry. Thus, for example, the non-proteinogenic piperazinecarboxylic acid in (S) configuration of the formula II

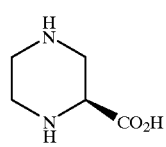

Formula II is an intermediate compound of the HIV proteinase inhibitor L-735,525 (*Tetrahedron Lett.* 1994, 35, 673–676) of the formula III.

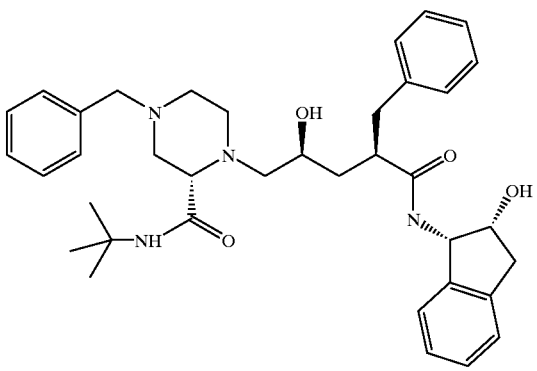

Formula III

DISCUSSION OF THE PRIOR ART

As is generally known to the person skilled in the art (J. Jacques, *Enantiomers, Racemates & Resolutions*, Wiley, N.Y., 1981), racemic compounds of the general formula I may be transformed into the diastereomeric salt pairs thereof in various solvents with optically active acids and separated by fractional crystallisation.

Synthesis of the chiral amino acid of the formula II is described, for example, in *Helv. Chim. Acta* 1960, 888–896 starting from aromatic, heterocyclic pyrazinecarboxylic acid. A key stage in the synthesis is the resolution of the racemic (R,S)-piperazinecarboxylic acid via diastereomeric salt pairs with the assistance of optically active (S)-camphorsulphonic acid [(S)-CSA] to yield the (S,S)-salt pair of the formula IV at a yield of only approx. 50% [relative to the diastereomeric pair (an exact yield could not be found in the above-stated literature reference)], i.e. at a total yield of approx. 25%.

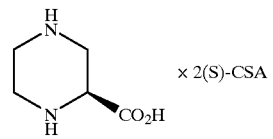

Formula IV

Apart from the moderate yields in conventional racemate resolution, an optical antipode is generally also obtained as a waste product on completion of a synthesis sequence, such that this method must be considered uneconomic or even unusable for industrial processes.

It is furthermore known that chiral α-amino acids may be racemised by adding catalytic quantities of aldehydes (*Tetrahedron Lett.* 1983, 24, 4457–4460), aldehydes and metal ions under alkaline conditions (JP 42-13445), and by heating in water under pressure (U.S. Pat. No. 3,213,106), in strong bases or acids (A. Neubergerin, M. L. Anson, J. T. Edsall, *Advances in Protein Chemistry*, Academic Press, New York 1948, 4, page 339) and in aliphatic carboxylic acids (*Chem. Pharm. Bull.* 1970, 18, 1788–1793). Disadvantages frequently associated with these stated racemisation methods are an excessively low rate of racemisation or the introduced α-amino acids undergo partial decomposition under the reaction conditions.

The object of the present invention is accordingly to provide a racemate resolution method for basic, cyclic, racemic amino acids which avoids the stated disadvantages and allows the corresponding optical antipodes to be obtained with the assistance of chiral acids at yields of above 50%, wherein attention should primarily be directed towards straightforward industrial implementation.

SUMMARY OF THE INVENTION

This object is achieved according to the invention by a) reacting the racemate of the basic, cyclic α-amino acid of the formula V

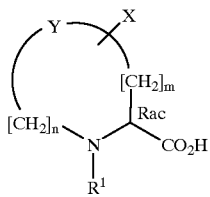

Formula V in which n, m, X, Y and $R^1$ have the above-stated meanings and Rac indicates that the adjacent carbon atom is racemic, b) with an optically active auxiliary acid to yield the salt pairs of the formula VI

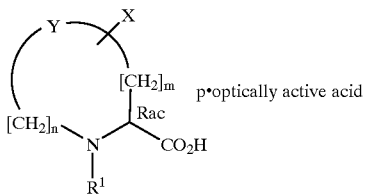

Formula VI in which n, m, X, Y, $R^1$ and Rac have the above-stated meanings and p states the molar ratio of the chiral acid to the α-amino acid, wherein p is dependent upon the number of basic centres and may be a number from 1 to 6, and c) separating a resultant diastereomeric salt pair of the formula VII

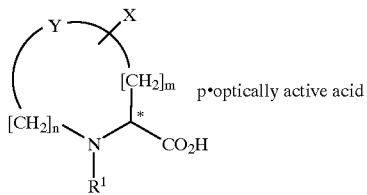

Formula VII in which n, m, X, Y, $R^1$, * and p have the above-stated meanings, from the mother liquor and d) combining and racemising the mother liquor with the corresponding chiral auxiliary acid used for resolving the racemate before subsequently making up the mother liquor e) with the racemate of the basic, cyclic amino acid of the formula V

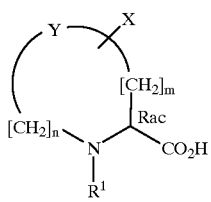

Formula V in which n, m, X, Y, Rac and $R^1$ have the above-stated meanings and, from the resultant diastereomeric salt pairs of the formula VI, f) again separating a diastereomeric salt pair of the formula VII

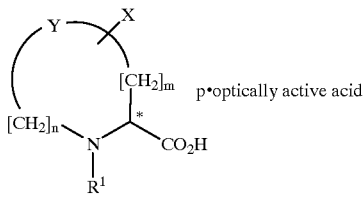

Formula VII in which n, m, X, Y, $R^1$, * and p have the above-stated meanings, from the mother liquor, combining this salt pair with the diastereomeric salt pair already obtained in c) and g) liberating the amino acid herefrom.

DISCUSSION OF THE PREFFERRED EMBODIMENTS

Surprisingly, according to the invention, the chiral auxiliary acid used for resolving the racemate may also be used for racemising a diastereomeric salt pair without any appreciable loss of chemical yield and chiral information. This is extremely unusual since, while firstly the reaction conditions and the excess of chiral amino acid do indeed racemise the α-amino acid or α-amino acid derivative, they do not racemise the chiral auxiliary acid itself. The reaction sequence d)–f) may advantageously be performed repeatedly in succession (continuously), which may also be achieved without appreciable loss of chemical yield and chiral information.

The present invention allows gentle reracemisation of the mother liquors by adding the corresponding chiral acids, elevated diastereomeric salt pair yields and recovery of the chiral auxiliary substances, as a consequence of which the process according to the invention is exceptionally economical.

The initial separation of the basic, racemic amino acids into the optical antipodes thereof using conventional racemate resolution via the corresponding diastereomeric salt pairs thereof proceeds in accordance with methods known per se (*Bull. Chem. Soc. Jpn.* 1989, 62, 109–113). To this end, the racemate of the formula I is dissolved, for example, in water, acetone, esters, such as for example methyl acetate, ethyl acetate, isopropyl acetate, or alcohols, such as for example methanol, ethanol, isopropanol, n-butanol, tert.-butanol, or a mixture of the stated solvents or another polar solvent, preferably in water, and is combined with 1–10 equivalents, preferably with 1–6 equivalents, of a chiral auxiliary acid, for example enantiomers of malic acid, lactic acid, tartaric acid, O,O'-dibenzoyltartaric acid, ditoluyltartaric acid (sic), pyroglutamic acid, bromocamphorsulphonic acid, camphorsulphonic acid or mandelic acid. The crystallised diastereomeric salt pair is separated from the mother liquor and may be recrystallised to purify it.

An amount corresponding to the weight percentage or a multiple thereof of the chiral auxiliary acid removed from the mother liquor by crystallisation of the diastereomeric salt pair is then added to the mother liquor, of the racemate resolution solution and the portion of the α-amino acid or the α-amino acid derivative remaining in the reaction solution is reracemised optionally at temperatures of between 120° C. and 25° C., preferably between 70° C. and 30° C. In the case of amino acids which are difficult to racemise, it may be advantageous to add 0.01–3 equivalents, preferably 0.05–0.1 equivalents, of an aldehyde, such as for example salicylaldehyde or benzaldehyde, to the reaction solution.

The solution is then made up again with racemic amino acid or an amino acid derivative of the formula I to achieve the initial molar ratios or a multiple thereof and is optionally seeded with a salt pair of the identically handed configuration.

The corresponding chiral amino acid of the formula I is also liberated from the diastereomeric salt pair thereof of the formula V using methods known per se (*Helvetica Chim. Acta* 1960, 888–896). To this end, the diastereomeric salt of the formula VII is dissolved or suspended in water, acetone, esters, such as for example methyl acetate, ethyl acetate, isopropyl acetate, or alcohols, such as for example methanol, ethanol, isopropanol, n-butanol, tert.-butanol or a mixture of the stated (sic), but preferably in water, and treated with an inorganic base, such as for example sodium hydrogen carbonate, sodium carbonate or sodium hydroxide solution or an organic base, such as for example ammonia, triethylamine or N-methylmorpholine and the resultant amino acid of the formula I is further processed in solution or isolated by crystallisation.

The diastereomeric salt pair of the formula VII is preferably dissolved in $H_2O$ and separated in a manner known per se (c.f. *Helv. Chim. Acta* 1960, 888) using an ion exchanger.

The diastereomeric salt pair of the formula VII is particularly preferably dissolved in $H_2O$ and passed over a basic ion exchanger, preferably over Amberlite IR-120®. While the amino acid is adsorbed on this ion exchanger and subsequently liberated in a known manner, the chiral auxiliary acid may be recovered directly in this manner.

The chiral auxiliary acid may accordingly be virtually entirely recycled by a simple preparative means, which is of great significance to the overall process on cost and environmental grounds.

The compounds of the structure of type I are known from the literature and may be produced in an analogous manner to *Helvetica Chim. Acta* 1960, 888–896.

The following Examples are intended to clarify the method described, but not to limit it thereto.

PRACTICAL EXAMPLES

Example 1

(S)-piperazinecarboxylic acid×2(S)-CSA 120.3 g (515 mmol, 2.3 eq.) of (S)-camphorsulphonic acid [(S)-CSA] are added in portions to a solution, heated to 70° C., of 29.3 g (225 mmol) of (R,S)-piperazinecarboxylic acid and 170 ml of $H_2O$. Once the yellowish solution has been provided with seed crystals [(S,S)-diastereomer], the solution is left to crystallise for approx. 16 hours. The resultant hard, colourless crystals are removed by suction filtration and washed with 20 ml of technical grade EtOH (N.B. Do not combine the ethanolic washing solution with the mother liquor.). The diastereomer ratio of the crystallised product [diastereomeric salt pair with (S,S)-configuration] is determined by chiral HPLC. Once the crystals have been dried, 32.7 g of product are obtained. The mother liquor is then made up with 25.6 g of (S)-CSA and refluxed for 6 hours. 7.15 g of racemic (R,S)-piperazinecarboxylic acid are then added to the hot mixture (70–90° C.) and the mixture allowed to cool to room temperature. The mixture is reseeded, left to crystallise and worked up in a similar manner to the above. These sequences are then performed another four times, the results of which are shown below.

| Sequence | Chemical yield of (S,S)-diastereomer [%] | dv value [(S,S):(R,S)]* |
|---|---|---|
| 1 | 46 | 99.7:0.3 |
| 2 | 42 | 99.5:0.5 |
| 2 (sic) | 40 | 99.5:0.5 |
| 4 | 49 | 99.7:0.3 |
| 5 | 42 | 99.7:0.3 |
| 6 | 42 | 99.3:0.7 |

*determined by chiral HPLC.

Purity: >95% by $^1$H-NMR.

Example 2

(S)-piperazinecarboxylic acid 71.4 g (120 mmol) of (S)-piperazinecarboxylic acid×2 (S)-CSA are dissolved in 300 ml of $H_2O$ and passed over the cation exchanger Amberlite IR 120® (480 ml). The ion exchanger is then washed to neutrality, the eluates evaporated to dryness and, after vacuum drying, 54.1 g (97%) of enantiomerically pure (S)-camphorsulphonic acid are recycled. The ion exchanger is then eluted in succession with 1.2 l of 5% $NH_3$ solution and $H_2O$. The combined eluates are evaporated to dryness. The resultant colourless solid is dissolved in approx. 50 ml of hot $H_2O$ and the product precipitated by stirring with technical grade ethanol. The free enantiomerically pure amino acid is removed by suction filtration and dried at 60° C. in a vacuum drying cabinet.

| | |
|---|---|
| Yield: | 15.14 g (97%) |
| Purity: | >95% by $^1$H-NMR. |
| Enantiomeric purity: | >99%. |

What is claimed is:

1. A process for the production of basic, cyclic and optically active a-amino acids of formula I

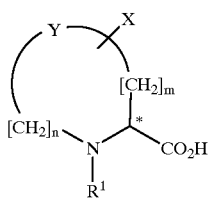

Formula I wherein
n, m are integers selected from the group consisting of 0, 1, 2 and 3,
Y is $CHR^1$, $NR^1$ or O
$R^1$ is H, benzyl, formyl, $COR^2$ or $CO_2R^2$
$R^2$ is $(C_1-C_6)$ alkyl or benzyl,
$R^3$ is $(C_1-C_6)$ alkyl or benzyl,
* Denotes a carbon atom in R or S configuration,
comprising the sequential steps of
  a) reacting the racemate of the basic, cyclic 1-amino acid of the formula V

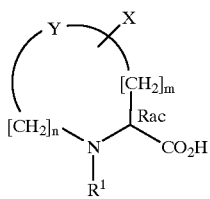

Formula V wherein Rac indicates that the adjacent carbon atom is racemic, with an optically active auxiliary acid to yield the salt pairs of the formula VI Formula VI

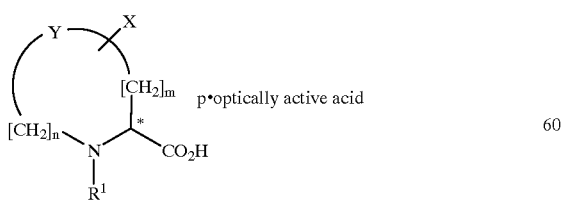

wherein p is an integer from 1 to 6, corresponds to the number of basic centers and is the molar ratio of the chiral acid to the a-amino acid and,
  b) separating a resultant diastereomeric salt pair of the formula VII from the mother liquor Formula VII

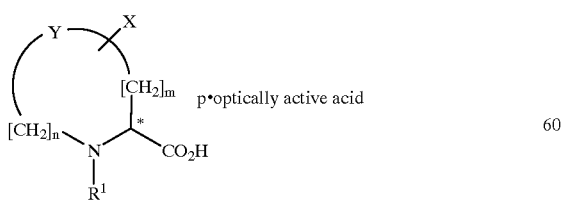

c) combining and racemnizing the mother liquor with the corresponding chiral auxiliary acid used for resolving the racemate d) Subsequently combining the thus combined and racemized mother liquor with the racemate of the basic, cyclic amino acid of the formula V

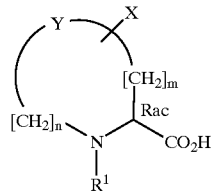

Formula V to provide the diastereomeric salts pairs of the formula VI,

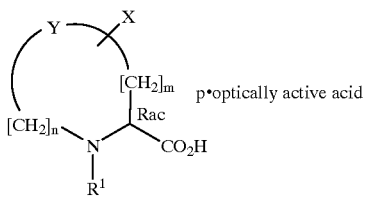

Formula VI e) Separating a diastereomeric salt pair of the formula VII again from the mother liquor of the previous step
  f) Combining this salt pair with the diastereomeric salt pair already obtained in b) and
  g) Liberating the amino acid therefrom.

2. The process according to claim 1, wherein
  (R,S)-piperazinecarboxylic acid is the α-amino acid and (S)-camphorsulphonic acid is the chiral auxiliary acid.

3. The process according to claim 1, wherein
  the reaction sequence c)–e) is carried out repeatedly.

4. The process according to claim 1, wherein
  the solvent used for the fractional crystallisation of the diastereomeric salt pairs selected from the group consisting of water, acetone, esters, alcohols, or a mixture of the said solvents.

5. The process according to claim 1, wherein the optically active acid used for resolving the racemate is selected from the group consisting of
  enantiomers of malic acid, lactic acid, tartaric acid,
  O,O'-dibenzoyltartaric acid, ditolyltartaric acid, pyroglutamic acid, bromocamphorsulphonic acid, camphorsulphonic acid and mandelic acid.

6. The process according to claim 1, comprising racemising the amino acid or amino acid derivative of the salt pair remaining in the mother liquor of step e) by adding the optically active acid which was removed from the reaction solution by crystallisation of the diastereomeric salt pair.

7. The process according to claim 1, comprising
  racemising the amino acid or amino acid derivative of the salt pair remaining in the mother liquor at temperatures of between 120° C. and 25° C.

8. The process according to claim 1, comprising adding
  an aldehyde to the mother liquor during racemisation of the α-amino acids or α-amino acid derivatives.

9. The process according to claim 8, comprising adding
  0.1–3 equivalents of aldehyde.

10. The process according to claim 4, wherein the solvent used for the fractional crystallisation of the diastereomeric salt pairs is selected from the group consisting of water, acetone, methyl acetate, ethyl acetate, isopropyl acetate, methanol, ethanol, isopropanol, n-butanol, tert-butanol, and a mixture of the said solvents.

11. The process according to claim 7, wherein the temperature of racemisation of the amino acid or amino acid derivative of the salt pair remaining in the mother liquor is between 70° C. and 30° C.

12. The process according to claim 8, wherein the aldehyde is salicyl- or benzaldehyde.

13. The process according to claim 12, wherein 0.05–1 equivalents, of aldehyde are added.

* * * * *